United States Patent
Sui et al.

(10) Patent No.: US 10,800,963 B2
(45) Date of Patent: Oct. 13, 2020

(54) PRESSURE-REDUCING AND INJECTION-ENHANCING ANTI SCALING AGENT FOR LOW-PERMEABILITY WATER-INJECTION WELL AND PREPARATION METHOD THEREOF

(71) Applicant: PetroChina Company Limited, Beijing (CN)

(72) Inventors: Lei Sui, Beijing (CN); Suiwang Zhang, Beijing (CN); Xiaobing Lu, Beijing (CN); Hongjun Lu, Beijing (CN); Lijun Mu, Beijing (CN); Yong Wang, Beijing (CN); Zhaojie Song, Beijing (CN); Zhiying Deng, Beijing (CN); Erzhen Wang, Beijing (CN)

(73) Assignee: PetroChina Company Limited, Beijing (CN)

( * ) Notice: Subject to any disclaimer, the term of this patent is extended or adjusted under 35 U.S.C. 154(b) by 75 days.

(21) Appl. No.: 15/857,916

(22) Filed: Dec. 29, 2017

(65) Prior Publication Data
US 2018/0187067 A1    Jul. 5, 2018

(30) Foreign Application Priority Data

Dec. 29, 2016 (CN) .......................... 2016 1 1242547

(51) Int. Cl.
| | | |
|---|---|---|
| C09K 8/584 | (2006.01) | |
| E21B 43/16 | (2006.01) | |
| C07F 9/38 | (2006.01) | |
| C07C 55/24 | (2006.01) | |
| C07C 229/04 | (2006.01) | |
| C07F 9/09 | (2006.01) | |
| C09K 8/528 | (2006.01) | |

(52) U.S. Cl.
CPC .............. *C09K 8/584* (2013.01); *C07C 55/24* (2013.01); *C07C 229/04* (2013.01); *C07F 9/091* (2013.01); *C07F 9/3808* (2013.01); *C07F 9/3873* (2013.01); *C09K 8/528* (2013.01); *E21B 43/16* (2013.01); *C09K 2208/12* (2013.01); *C09K 2208/32* (2013.01)

(58) Field of Classification Search
CPC .................................. C09K 8/584; C09K 8/528
See application file for complete search history.

(56) References Cited

FOREIGN PATENT DOCUMENTS

| | | |
|---|---|---|
| CN | 101798502 A | 8/2010 |
| CN | 101993685 A | 3/2011 |
| CN | 102634332 A | 8/2012 |
| CN | 102703045 A | 10/2012 |
| CN | 102730872 A | 10/2012 |
| CN | 103394289 A | 11/2013 |
| CN | 103820150 A | 5/2014 |

OTHER PUBLICATIONS

Li Pengfei et al. "The Development in Research of polyaspartic Acid as Environment-friendly Water Treatment Chemicals," Chenmical Intermediate, No. 1, 2013.
First Office Action and search report dated Feb. 12, 2019 for counterpart Chinese patent application No. 201611242547.8, along with machine EN translation.
Second Office Action dated Dec. 3, 2019 for counterpart Chinese patent application No. 201611242547.8, along with machine English Language translation.
Decision of Rejection dated May 8, 2020 for counterpart Chinese patent application No. 201611242547.8, along with machine EN translation.

*Primary Examiner* — Peter F Godenschwager
(74) *Attorney, Agent, or Firm* — Meunier Carlin & Curfman LLC

(57) ABSTRACT

The present disclosure provides a pressure-reducing and injection-enhancing anti-scaling agent for low-permeability water-injection wells and a preparation method thereof. The anti-scaling agent is prepared from starting materials comprising: 10 to 12 parts of non-ionic surfactant(s), 18 to 20 parts of hexasodium triethylenetetramine-N,N,N',N'',N''',N'''-hexaacetate, 5 to 8 parts of anionic surfactant(s), 6 to 8 parts of an organic phosphonic acid-carboxylic acid scale inhibitor, 2 to 5 parts of a dispersant, 15 to 18 parts of a diluent, 8 to 10 parts of an organic amine salt, and 30 to 36 parts of water. The pressure-reducing and injection-enhancing agent according to the present disclosure is characterized by having multiple functions in one agent. When used in an amount being 0.5% of the water injected to a water injection well, it shows excellent anti-swelling property, shrinking property, anti-corrosive property, and calcium sulfate and barium (strontium) sulfate scale resistance.

15 Claims, No Drawings

PRESSURE-REDUCING AND INJECTION-ENHANCING ANTI SCALING AGENT FOR LOW-PERMEABILITY WATER-INJECTION WELL AND PREPARATION METHOD THEREOF

TECHNICAL FIELD

Embodiments of the present disclosure relate to the technical field of oil exploitation, particularly to an anti-scaling technique for oil exploitation, and more particularly, to a pressure-reducing and injection-enhancing anti-scaling agent for low-permeability water-injection well and a preparation method thereof.

BACKGROUND

Low-permeability oil reservoirs have poor physical properties, mainly in that their reservoir structure has low porosity and poorly permeable fine channels, as well as a high content of cement. These physical properties lead to high pressure and difficulty in water injection into the wells The problems of difficulty and high pressure in water injection are common in exploitation of low-permeability oil reservoirs, and the reason therefor has been analyzed. The fundamental reason lies in the threshold pressure gradient of low (ultra-low) permeability oil reservoirs, which must be overcome during water injection to establish an effective displacement pressure difference for the purpose of oil displacement. Low-permeability reservoirs have seepage flow characteristics different from those of general medium-to-high permeability reservoirs. The fine pores and channels and poor physical properties of low-permeability reservoirs, and the effects of surface molecular force and capillary force on the seepage flow through low-permeability reservoirs, often result in high injection pressure and thus difficulty in water injection. Furthermore, because the injected water has low water quality, a high degree of mineralization, and high contents of calcium and magnesium ions, secondary contamination due to the poor water quality further damages the oil reservoirs, and the injection pressure increases over time.

SUMMARY

An objective of the present disclosure is to provide a pressure-reducing and injection-enhancing anti-scaling agent for low-permeability water-injection wells. The anti-scaling agent according to the present disclosure can resolve the problem caused by insoluble scales of calcium sulfate, barium sulfate and strontium sulfate that cannot be resolved by conventional chemical methods, can clean up the accumulated scales around a water injection well and inside the pipes, establish new pores and flow channels, restore permeability of oil and gas, and achieve pressure reduction and injection enhancement for water-injection wells.

Another objective of the present disclosure is to provide a method for preparing the pressure-reducing and injection-enhancing anti-scaling agent for low-permeability water-injection wells.

For the above objectives, the present disclosure provides in one aspect a pressure-reducing and injection-enhancing anti-scaling agent for low-permeability water-injection wells, which is prepared from starting materials comprising the following components: 10 to 12 parts of non-ionic surfactant(s), 18 to 20 parts of hexasodium triethylenetetramine-N,N,N',N'',N''',N'''-hexaacetate, 5 to 8 parts of anionic surfactant(s), 6 to 8 parts of an organic phosphonic acid-carboxylic acid scale inhibitor, 2 to 5 parts of a dispersant, 15 to 18 parts of a diluent, 8 to 10 parts of an organic amine salt, and 30 to 36 parts of water.

In some particular embodiments of the present disclosure, the anti-scaling agent is prepared from starting materials comprising the following components: 11 parts of non-ionic surfactant(s), 18 parts of hexasodium triethylenetetramine-N,N,N',N'',N''',N'''-hexaacetate, 6 parts of anionic surfactant(s), 6 parts of an organic phosphonic acid-carboxylic acid scale inhibitor, 3 parts of a dispersant, 16 parts of a diluent, 8 parts of an organic amine salt, and 35 parts of water.

In some particular embodiments of the present disclosure, the non-ionic surfactant is a polyoxyethylene non-ionic surfactant.

In some particular embodiments of the present disclosure, the non-ionic surfactant is a fatty alcohol polyoxyethylene ether, a polyoxyethylene octylphenol ether, or a polyoxyethylene nonyl phenyl ether.

In some particular embodiments of the present disclosure, the anionic surfactant is a water-soluble phosphate-based anionic fluorocarbon surfactant.

In some particular embodiments of the present disclosure, the water-soluble phosphate-based anionic fluorocarbon surfactant has a structural formula of $(RfCH_2CH_2O)nPO(ONH_4)m$, wherein $Rf=F(CF_2CF_2)x$, $n+m=3$, and $x=1$ to 7, and having a molecular weight of 500 to 600.

The water-soluble phosphate-based anionic fluorocarbon surfactant is commercially available. Any commercially available water-soluble phosphate-based anionic fluorocarbon surfactants satisfying the above characteristics (i.e. having a structural formula of $(RfCH_2CH_2O)nPO(ONH_4)m$, wherein $Rf=F(CF_2CF_2)x$, $n+m=3$, and $x=1$ to 7, and having a molecular weight of 500 to 600) can be used in the present disclosure, for example, the water-soluble phosphate-based anionic fluorocarbon surfactant Zonyl® FSP manufactured by DuPont, USA.

In some particular embodiments of the present disclosure, the organic phosphonic acid-carboxylic acid scale inhibitor is 2-phosphonobutane-1,2,4-tricarboxylic acid or sodium ethylenebis(nitrilobismethylene)tetraphosphonate.

In some particular embodiments of the present disclosure, the dispersant is monobutyl ethylene glycol ether or dibutyl ethylene glycol ether.

In some particular embodiments of the present disclosure, the diluent is methanol, ethanol, or ethylene glycol.

In some particular embodiments of the present disclosure, the organic amine salt is monoethanolamine, triethanolamine, or diethylene diamine.

In another aspect, the present disclosure provides a method for preparing the pressure-reducing and injection-enhancing anti-scaling agent for low-permeability water-injection wells, comprising the steps of: weighing the components; sequentially adding the organic phosphonic acid-carboxylic acid scale inhibitor, the anionic surfactant(s) and the non-ionic surfactant(s) to water; then adding the organic amine salt and hexasodium triethylenetetramine-N,N,N',N'', N''',N'''-hexaacetate under stirring to allow a reaction to proceed; after the reaction is complete, adding the diluent and dispersant; and collecting the product to obtain the anti-scaling agent.

In some particular embodiments of the present disclosure, in the method, the step of adding the organic amine salt and hexasodium triethylenetetramine-N,N,N',N'',N''',N'''-hexaacetate is performed under stirring at 40 to 60 rpm, before the reaction.

In some particular embodiments of the present disclosure, after adding the organic amine salt and hexasodium triethylenetetramine-N,N,N',N'',N''',N'''-hexaacetate, the reaction is carried out at 80 to 90° C.

In some particular embodiments of the present disclosure, after adding the organic amine salt and hexasodium triethylenetetramine-N,N,N',N'',N''',N'''-hexaacetate, the reaction is allowed to proceed for 2 to 5 hours, before addition of the diluent and dispersant.

In some particular embodiments of the present disclosure, after the reaction is complete, the temperature is decreased to room temperature, before addition of the diluent and dispersant.

In summary, embodiments of the present disclosure provide a pressure-reducing and injection-enhancing anti-scaling agent for low-permeability water-injection wells and a method for preparing it. The anti-scaling agent according to the present disclosure has the following advantages.

The pressure-reducing and injection-enhancing anti-scaling agent for low permeability water-injection wells according to the present disclosure is characterized by having multiple functions in one agent. When used in an amount being 0.5% of the water injected to a water-injection well, it shows excellent anti-swelling property, shrinking property, anti-corrosive property, and calcium sulfate and barium (strontium) sulfate scale resistance. At 60° C., the solubility of barium sulfate is increased by 3125 times. The anti-scale agent prevents corrosion and scaling in the water injection system for oil fields to a greater extent, extends the lifetime of equipment and pipes, ensures effective operation of previous production, and increases the recovery ratio from oil reservoirs.

DETAILED DESCRIPTION

The embodiments and beneficial effects of the present disclosure will be described in detail in conjunction with Examples, in order to help readers better understand the nature and features of the present disclosure, but the Examples do not limit the implementable scope of the present disclosure.

Example 1

The example provides a pressure-reducing and injection-enhancing anti-scaling agent for low-permeability water-injection wells, which consists of the following starting materials in parts by weight: 11 parts of non-ionic surfactant(s), 19 parts of hexasodium triethylenetetramine-N,N,N',N'',N''',N'''-hexaacetate, 6 parts of anionic surfactant(s), 7 parts of an organic phosphonic acid-carboxylic acid scale inhibitor, 4 parts of a dispersant, 16 parts of a diluent, 9 parts of an organic amine salt, and 32 parts of water.

Preparation method: to a dry enamel reaction kettle, water 320 kg, organic phosphonic acid-carboxylic acid scale inhibitor 70 kg, anionic fluorocarbon surfactant 60 kg, and non-ionic surfactant 110 kg were added in this order; a stirrer was initiated, and organic amine salt 90 kg and hexasodium triethylenetetramine-N,N,N',N'',N''',N'''-hexaacetate 190 kg were added under stirring; the mixture was heated to 80° C. to react for 2 hours, and then cooled to room temperature; diluent 160 kg and dispersant 40 kg were added; and the product was collected to give the high-performance pressure-reducing and injection-enhancing agent for low-permeability water-injection wells as a commercial product.

In this Example, the non-ionic surfactant is a fatty alcohol polyoxyethylene ether AEO-9; hexasodium triethylenetetramine-N,N,N',N'',N''',N'''-hexaacetate; the anionic surfactant is $(RfCH_2CH_2O)nPO(ONH_4)m$, wherein $Rf=F(CF_2CF_2)x$, $n+m=3$, and $x=1$ to $7$, having a molecular weight of 500 to 600; the organic phosphonic acid-carboxylic acid scale inhibitor is 2-phosphonobutane-1,2,4-tricarboxylic acid, the dispersant is monobutyl glycol ether; the diluent is methanol; and the organic amine salt is monoethanolamine.

The present disclosure combines an organic phosphonic acid-carboxylic acid scale inhibitor with hexasodium triethylenetetramine-N,N,N',N'',N''',N'''-hexaacetate to obtain an agent which has excellent anti-scaling and dispersing performance against calcium carbonate, calcium sulfate, barium sulfate, calcium fluoride and silicon-based scales in water, and very easily adsorbs microcrystalline sulfate scale on a surface physically and chemically to greatly improve the solubility of the sulfate scale. In practical production, since the surface of scales often has a layer of oily soil adhered thereon, washing with non-ionic and anionic surfactants and an organic amine salt ensures sufficient contact between the agent and the scales. The present disclosure uses methanol and monobutyl glycol ether as dispersant and diluent, to ensure that active components act on rock surfaces more rapidly.

Example 2

The example provides a pressure-reducing and injection-enhancing anti-scaling agent for low permeability water injection wells, which consists of the following starting materials in parts by weight: 10 parts of non-ionic surfactant(s), 18 parts of hexasodium triethylenetetramine-N,N,N',N'',N''',N'''-hexaacetate, 5 parts of anionic surfactant(s), 6 parts of an organic phosphonic acid-carboxylic acid scale inhibitor, 2 parts of a dispersant, 15 parts of a diluent, 8 parts of an organic amine salt, and 30 parts of water.

Preparation method: to a dry enamel reaction kettle, water 300 kg, organic phosphonic acid-carboxylic acid scale inhibitor 60 kg, anionic fluorocarbon surfactant 50 kg, and non-ionic surfactant 100 kg were added in this order; a stirrer was started, and organic amine salt 80 kg and hexasodium triethylenetetramine-N,N,N',N'',N''',N'''-hexaacetate 180 kg were added under stirring; the mixture was heated to 80° C. to react for 3 hours, and then cooled to room temperature; diluent 150 kg and dispersant 20 kg were added; and the product was collected to give the high-performance pressure-reducing and injection-enhancing agent for low permeability water injection wells as a commercial product.

In this Example, the non-ionic surfactant is a polyoxyethylene octylphenol ether OP-10; hexasodium triethylenetetramine-N,N,N',N'',N''',N'''-hexaacetate; the anionic surfactant is $(RfCH_2CH_2O)nPO(ONH_4)m$, wherein $Rf=F(CF_2CF_2)x$, $n+m=3$, and $x=1$ to $7$, having a molecular weight of 500 to 600; the organic phosphonic acid-carboxylic acid scale inhibitor is sodium ethylenebis(nitrilobismethylene) tetraphosphonate, the dispersant is dibutyl glycol ether; the diluent is ethanol; and the organic amine salt is triethanolamine.

Example 3

The example provides a pressure-reducing and injection-enhancing anti-scaling agent for low permeability water injection wells, which consists of the following starting materials in parts by weight: 12 parts of non-ionic surfactant(s), 20 parts of hexasodium triethylenetetramine-N,N,N',N'',N''',N'''-hexaacetate, 8 parts of anionic surfactant(s), 8 parts of an organic phosphonic acid-carboxylic acid scale inhibitor, 5 parts of a dispersant, 15-18 parts of a diluent, 10 parts of an organic amine salt, and 36 parts of water.

Preparation method: to a dry enamel reaction kettle, water 360 kg, organic phosphonic acid-carboxylic acid scale inhibitor 80 kg, anionic fluorocarbon surfactant 80 kg, and non-ionic surfactant 120 kg were added in this order; a stirrer was started, and organic amine salt 100 kg and hexasodium triethylenetetramine-N,N,N',N'',N''',N'''-hexaacetate 200 kg were added under stirring; the mixture was heated to 80° C. to react for 4 hours, and then cooled to room temperature; diluent 180 kg and dispersant 50 kg were added; and the product was collected to give the high-performance pressure-reducing and injection-enhancing agent for low permeability water injection wells as a commercial product.

In this Example, the non-ionic surfactant is a polyoxyethylene nonyl phenyl ether TX-10; hexasodium triethylenetetramine-N,N,N',N'',N''',N'''-hexaacetate; the anionic surfactant is $(RfCH_2CH_2O)nPO(ONH_4)m$, wherein $Rf=F(CF_2CF_2)x$, $n+m=3$, and $x=1$ to 7, having a molecular weight of 500 to 600; the organic phosphonic acid-carboxylic acid scale inhibitor is sodium ethylenebis(nitrilobismethylene)tetraphosphonate, the dispersant is dibutyl glycol ether; the diluent is ethylene glycol; and the organic amine salt is diethylene diamine.

Example 4

The example provides a pressure-reducing and injection-enhancing anti-scaling agent for low permeability water injection wells, which consists of the following starting materials in parts by weight: 11 parts of non-ionic surfactant(s), 18 parts of hexasodium triethylenetetramine-N,N,N',N'',N''',N'''-hexaacetate, 6 parts of anionic surfactant(s), 6 parts of an organic phosphonic acid-carboxylic acid scale inhibitor, 3 parts of a dispersant, 16 parts of a diluent, 8 parts of an organic amine salt, and 35 parts of water.

Preparation method: to a dry enamel reaction kettle, water 350 kg, organic phosphonic acid-carboxylic acid scale inhibitor 60 kg, anionic fluorocarbon surfactant 60 kg, and non-ionic surfactant 110 kg were added in this order; a stirrer was started, and organic amine salt 80 kg and hexasodium triethylenetetramine-N,N,N',N'',N''',N'''-hexaacetate 180 kg were added under stirring; the mixture was heated to 80° C. to react for 5 hours, and then cooled to room temperature; diluent 160 kg and dispersant 30 kg were added; and the product was collected to give the high-performance pressure-reducing and injection-enhancing agent for low permeability water injection wells as a commercial product.

In this Example, the non-ionic surfactant is a polyoxyethylene nonyl phenyl ether TX-10; hexasodium triethylenetetramine-N,N,N',N'',N''',N'''-hexaacetate; the anionic surfactant is $(RfCH_2CH_2O)nPO(ONH_4)m$, wherein $Rf=F(CF_2CF_2)x$, $n+m=3$, and $x=1$ to 7, having a molecular weight of 500 to 600; the organic phosphonic acid-carboxylic acid scale inhibitor is 2-phosphonobutane-1,2,4-tricarboxylic acid, the dispersant is monobutyl glycol ether; the diluent is ethanol; and the organic amine salt is monoethanolamine.

The technical parameters of quality of the high-performance pressure-reducing and injection-enhancing agent for low-permeability water-injection wells prepared in Examples 1-4 of the present disclosure are as follows:

Appearance: colorless transparent liquid at room temperature;

pH: 9 to 12;

Anti-swelling ratio: 60% or higher, tested according to SY/T 5971 "Method for evaluating the performance of clay stabilizer for water injection";

Shrinkage ratio: 30% or higher;

Anti-scaling ratio: 95% or higher against calcium sulfate; 90% or higher against barium (strontium) sulfate; tested according to Q/SY 126-2014 "Technical requirements for anti-corrosion scale inhibitor for water treatment of oil fields";

Corrosion rate: 0.021 mm/a or lower; according to SY/T 5273-2014 "Criteria and evaluation method for performance of anti-corrosion agent for water treatment of oil field products";

Solubility of barium sulfate at 60° C.: 0.8 g/100 g or higher.

When used in an amount being 0.5% of the water injected to a water injection well, it shows excellent anti-swelling property, shrinking property, anti-corrosive property, and calcium sulfate and barium (strontium) sulfate scale resistance. At 60° C., the solubility of barium sulfate is increased by 3125 times.

An on-site test using the high-performance pressure-reducing and injection-enhancing agent for low-permeability water-injection wells prepared in Example 4 was performed as follows.

The high-performance pressure-reducing and injection-enhancing agent for low permeability water injection wells was tested on site in the No. x-xx well of the X oil exploitation plant in Changqing oil field. The average permeability is 3 MD, sensitive to weak acids. Over the first 10 months of injection, the water absorbing index dropped from 3.1 m³/d·MPa to 1.1 m³/d·MPa, and the corrosion rate dropped from 0.082 mm/a to 0.036 mm/a. The formation water of the oil field contained approximately 3,000 mg/L barium (strontium) ions, and the water for injection is of a sodium sulfate type, which are very incompatible to each other and easily produce carbonate or sulfate precipitates in formation layers, which is one of the major reasons responsible for reservoir plugging. An unplugging process using the high-performance pressure-reducing and injection-enhancing agent for low-permeability water-injection wells was applied. After the unplugging process, the water absorbing index started to increase and stabilized at the level of 3.3 m³/d·MPa, and the daily injection amount of water was increased from 18 m³ to 39 m³, which remained effective for over 2.1 years without a pump checking operation due to scaling.

In summary, the high-performance pressure-reducing and injection-enhancing agent for low-permeability water-injection wells according to the present disclosure is characterized by having multiple functions in one agent. As compared to the anti-scaling agents in the prior art, the present agent combines the product of the reaction between an organic phosphonic acid-carboxylic acid scale inhibitor and an organic amine with hexasodium triethylenetetramine-N,N,N',N'',N''',N'''-hexaacetate, which results in excellent anti-scaling and anti-corrosive performance, and makes the agent very easily adsorb microcrystalline sulfate scale on a surface physically and chemically to greatly improve the solubility of the sulfate scale. In practical production, since the surface of scales often has a layer of oily soil adhered thereon, washing with non-ionic and anionic surfactants and an organic amine salt ensures sufficient contact between the agent and the scales, while the dispersant and diluent can ensure that active components act on rock surfaces more rapidly. When used in an amount of 0.5%, it shows excellent anti-swelling property, shrinking property, anti-corrosive property, and calcium sulfate and barium (strontium) sulfate scale resistance. At 60° C., the solubility of barium sulfate is increased by 3125 times. The agent prevents and suppresses corrosion and scaling in the water injection system for oil fields to a greater extent, extends the lifetime of equipment and pipes, ensures effective operation of prior production, and increases the recovery ratio from oil reservoirs.

Those test methods not described in detail in the above Examples are common knowledge in the art, and specified description thereof is omitted here.

The invention claimed is:

1. A pressure-reducing and injection-enhancing anti-scaling agent for low-permeability water-injection wells, prepared from starting materials comprising the following components:
   10 to 12 parts of non-ionic surfactant(s),
   18 to 20 parts of hexasodium triethylenetetramine-N,N,N',N'',N''',N''''-hexaacetate,
   5 to 8 parts of anionic surfactant(s),
   6 to 8 parts of an organic phosphonic acid-carboxylic acid scale inhibitor,
   2 to 5 parts of a dispersant,
   15 to 18 parts of a diluent,
   8 to 10 parts of an organic amine salt, and
   30 to 36 parts of water.

2. The anti-scaling agent according to claim 1, prepared from starting materials comprising the following components:
   11 parts of non-ionic surfactant(s),
   18 parts of hexasodium triethylenetetramine-N,N,N',N'',N''',N''''-hexaacetate,
   6 parts of anionic surfactant(s),
   6 parts of an organic phosphonic acid-carboxylic acid scale inhibitor,
   3 parts of a dispersant,
   16 parts of a diluent,
   8 parts of an organic amine salt, and
   35 parts of water.

3. The anti-scaling agent according to claim 1, wherein the non-ionic surfactant is a polyoxyethylene non-ionic surfactant.

4. The anti-scaling agent according to claim 3, wherein the non-ionic surfactant is a fatty alcohol polyoxyethylene ether, a polyoxyethylene octylphenol ether, or a polyoxyethylene nonyl phenyl ether.

5. The anti-scaling agent according to claim 1, wherein the anionic surfactant is a water-soluble phosphate-based anionic fluorocarbon surfactant.

6. The anti-scaling agent according to claim 5, wherein the anionic surfactant is a water-soluble phosphate-based anionic fluorocarbon surfactant having a structural formula of $(RfCH_2CH_2O)nPO(ONH_4)m$, wherein $Rf=F(CF_2CF_2)x$, $n+m=3$, and $x=1$ to 7, and having a molecular weight of 500 to 600.

7. The anti-scaling agent according to claim 1, wherein the organic phosphonic acid-carboxylic acid scale inhibitor is 2-phosphonobutane-1,2,4-tricarboxylic acid or sodium ethylenebis(nitrilobismethylene)tetraphosphonate.

8. The anti-scaling agent according to claim 1, wherein the dispersant is monobutyl ethylene glycol ether or dibutyl ethylene glycol ether.

9. The anti-scaling agent according to claim 1, wherein the diluent is methanol, ethanol, or ethylene glycol.

10. The anti-scaling agent according to claim 1, wherein the organic amine salt comprises monoethanolamine, triethanolamine, or diethylene diamine.

11. A method for preparing the pressure-reducing and injection-enhancing anti-scaling agent for low-permeability water-injection wells of claim 1, said method comprising the steps of:
    weighing the components;
    adding the organic phosphonic acid-carboxylic acid scale inhibitor, the anionic surfactant and the non-ionic surfactant to water;
    then adding the organic amine salt and hexasodium triethylenetetramine-N,N,N',N'',N''',N''''-hexaacetate under stirring, to allow a reaction to proceed,
    after the reaction is complete, adding the diluent and the dispersant; and
    collecting the product to obtain the anti-scaling agent.

12. The method according to claim 11, further comprising: after the reaction is complete, lowering the temperature to room temperature, before addition of the diluent and the dispersant.

13. The method according to claim 11, wherein the method comprises adding the organic amine salt and hexasodium triethylenetetramine-N,N,N',N'',N''',N''''-hexaacetate under stirring at 40 to 60 rpm.

14. The method according to claim 11, wherein the reaction is carried out at 80 to 90° C.

15. The method according to claim 11, wherein the reaction is carried out for 2 to 5 hours.

* * * * *